United States Patent [19]

Liang et al.

[11] Patent Number: 5,633,401
[45] Date of Patent: May 27, 1997

[54] PROCESS FOR DECOLORIZING CYCLOPROPANECARBOXYLIC ACID

[75] Inventors: Shaowo Liang, Kingsport; Timothy W. Price, Church Hill, both of Tenn.

[73] Assignee: Eastman Chemical Company, Kingsport, Tenn.

[21] Appl. No.: 627,668

[22] Filed: Apr. 1, 1996

[51] Int. Cl.$^6$ .................................................. C07C 61/04
[52] U.S. Cl. ............................................................ 562/506
[58] Field of Search ............................................... 562/506

[56] References Cited

U.S. PATENT DOCUMENTS 5,504,245  4/1996  Laing ........................................ 562/506

Primary Examiner—Michael L. Shippen
Attorney, Agent, or Firm—J. Frederick Thomsen; Harry J. Gwinnell

[57] ABSTRACT

Disclosed is a process for the conversion of off-color cyclopropanecarboxylic acid (CPC-Acid) to CPC-Acid having a color value (platinum-cobalt scale) of less than about 10 by the steps of (1) heating off-color CPC-Acid produced by the oxidation of cyclopropanecarboxaldehyde with molecular oxygen with a strong acid; and (2) distilling the mixture of step (1) to obtain CPC-Acid having a color value of less than about 10 as the distillate product.

5 Claims, No Drawings

PROCESS FOR DECOLORIZING CYCLOPROPANECARBOXYLIC ACID

This invention pertains to a process for improving the color of cyclopropanecarboxylic acid (CPC-Acid) prepared by the oxidation of cyclopropanecarboxaldehyde. More specifically, this invention pertains to a process for decolorizing CPC-Acid which contains color bodies and is prepared by contacting cyclopropanecarboxaldehyde with molecular oxygen by contacting such CPC-Acid with an acid at elevated temperature and distilling the acid-treated CPC-Acid.

CPC-Acid its derivatives, especially cyclopropylamine, are useful in the synthesis of pharmaceuticals and pesticides. See, for example, European Patent Publications EP 237,955 A2, EP 273,862 A2 and EP 430,847 A1. The manufacture of CPC-Acid by the non-catalytic, oxidation of cyclopropanecarboxaldehyde is described in U.S. Pat. No. 5,504,245. Cyclopropanecarboxaldehyde may be obtained by the thermal isomerization or rearrangement of 2,3-dihydrofuran. For example, U.S. Pat. No. 4,275,238 describes passing 2,3-dihydrofuran through a column at 480° C. to obtain cyclopropanecarboxaldehyde having a purity of 90% purity and containing 6.2–6.7% crotonaldehyde. A similar procedure is described by Wilson, J. Amer. Chem. Soc. 69, 3002 (1947). 2,3-Dihydrofuran may be obtained according to the process described in U.S. Pat. No. 5,254,701 by the isomerization of 2,5-dihydrofuran which in turn can be produced by the isomerization of 3,4-epoxy-1-butene as described in U.S. Pat. Nos. 3,932,468, 3,996,248 and 5,082,956. U.S. Pat. Nos. 4,897,498 and 4,950,773 describe the preparation of 3,4-epoxy-1-butene by selective monoepoxidation of butadiene.

CPC-Acid manufactured of CPC-Acid by contacting cyclopropanecarboxaldehyde with molecular oxygen, normally in the absence of an oxidation catalyst, as described in U.S. Pat. No. 5,504,245 frequently contains color bodies which impart a yellow or brown color to the CPC-Acid, e.g., a color of 20 to 800 when measured on a platinum-cobalt scale (PCS, ASTM D 1209). It is not unusual that purified CPC-Acid having an assay (purity) greater than 99% has a color of 50 to 200 PCS which renders the CPC-Acid unsuitable for use in the manufacture of pharmaceuticals and other fine chemicals.

Prior art methods for removing color from organic compounds have involved heating, in general, with active carbon follow by filtration and distillation, or decolorizing by oxidation with peroxide(s) or by reduction with borohydride or catalytic hydrogenation. See, for example, Japanese Kokai JP 50130713 A; UK Published Patent Application GB 2,072,656 A; Japanese Kokai JP 48018213 A; U.S. Pat. No. 3,775,450. Color bodies are complicated impurities which vary depending upon the particular process in which they are generated. There is no known methods for the removal of color bodies generated by the oxidation of cyclopropyl-containing compounds. Due to the highly sensitive nature of cyclopropane ring, molecules containing a cyclopropyl ring are known to undergo ring opening under such oxidation conditions (J. Am. Chem. Soc., 1991, 113, 5687) and reduction conditions (J. Chem. Soc. Chem. Commun. 1968, 569 and Chem. Abstracts 59: 2749). Thus, these prior art methods are not suitable for removing color bodies from CPC-Acid.

We have found that when off-color CPC-Acid produced by the oxidation of cyclopropanecarboxaldehyde with molecular oxygen is heated in the presence of a strong acid, the color bodies responsible for the off-color are converted to materials which have boiling points significantly different from the boiling point of CPC-Acid. When the resulting mixture is subjected to distillation, substantially colorless CPC-Acid is recovered as the distillate. Our invention, therefore, provides a process for the conversion of off-color CPC-Acid to CPC-Acid having a color value of less than about 10 PCS by the steps of:

(1) heating off-color CPC-Acid produced by the oxidation of cyclopropanecarboxaldehyde with molecular oxygen with a strong acid; and (2) distilling the mixture of step (1) to obtain CPC-Acid having a color value of less than about 10 PCS as the distillate product;

wherein the color values are measured by ASTM Procedure D 1209. The process preferably is operated in a manner which produces CPC-Acid having a color value of 1 to 5 PCS.

The strong acids which may be used in the process have a pKa of about 4 or less, preferably about −8 to 3, and a boiling point higher than the boiling point of CPC-Acid (normal b.p. 182° C.). Examples of such acids include (1) inorganic acids such as sulfuric acid, phosphoric acid, polyphosphoric acid, nitric acid, hydrochloric acid and the like; (2) organic acids such as perfluorocarboxylic acids containing 2–4 carbon atoms, e.g., trifluoroacetic acid; alkylsulfonic acids containing 1–4 carbon atoms, e.g., methanesulfonic acid; arylsulfonic acids, e.g., benzenesulfonic acid and p-toluenesulfonic acid; perfluoroalkanesulfonic acids containing 1 to 4 carbon atoms, e.g., trifluoromethanesulfonic acid; and polymeric sulfonic acids, e.g., acidic ion exchange resins such as sulfo-substituted, styrene/divinylbenzene copolymers and perfluoro polymeric sulfonic acids. The preferred acids are organic sulfonic acids, especially the polymeric sulfonic acids which are not soluble in CPC-Acid and therefore can be separated, e.g., by filtration, prior to distillation and used in subsequent batches of the decolorization process. Suitable polymeric sulfonic acids are commercial products sold under the tradenames Amberlyst XN-1010, Amberlyst 15, Dowex 50 and Nafion-H.

The amount of strong acid required to produce a substantially colorless CPC-Acid varies substantially depending on a number of factor such as, for example, the particular acid used, the time and temperature used in heating the strong acid/CPC-Acid mixture, and the color of the off-color CPC-Acid be used in the decolorization process. The amount of acid usually is in the range of about 0.01 to 20 weight percent, preferably about 0.1 to 5 weight percent, based on the weight of the off-color CPC-Acid present. When using a preferred insoluble, polymeric sulfonic acid, the acid preferably is removed from the off-color CPC-Acid prior to distillation. When soluble strong acids are used, they are not removed prior to distillation.

The temperature used in the first step of the process typically is in the range of about 20° to 200° C. although color removal can be demonstrated at lower temperatures. The preferred temperatures are in the range of about 50° to 150° C. The first step may be carried out at pressures of 0.5 torr to 100 bar. Normally, when the process is operated in a batch mode wherein the strong acid/CPC-Acid mixture is first heated for a set period of time and then distilled, the acid treatment step is carried out at ambient pressure. The time required by the first step will vary depending upon such factors as the strong acid, the temperature and the color of the CPC-Acid used. Generally, strong acid/CPC-Acid contact times of about 10 to 300 minutes are sufficient to permit conversion of the color bodies in the CPC-Acid to materials which can be separated from the CPC-Acid by distillation.

The distillation of the second step may be carried out immediately after completion of the first step treatment or it may be carried out at some later time without any deterioration of the final product. The distillation may be performed at atmospheric (ambient) or reduced pressure, e.g. pressures of about 0.5 to 200 torr.

The process of this invention may be carried out in a batch, semicontinuous or continuous mode of operation. For example, one mode of operation comprises feeding off-color CPC-Acid in the absence of solvent or, optionally, in an inert solvent-diluent, to the top of a columnar reactor containing one or more fixed beds of solid resins. The reactant solution flows (trickles) over the resin bed at the desired temperature and the treated product exits the bottom of the reactor and is subjected to distillation to give substantially colorless CPC-Acid of greater than 99% purity. Another mode of operation involves heating a mixture of off-color CPC-Acid and a strong acid in a heated vessel equipped with a distillation column. Off-color CPC-Acid can be fed continuously fed to, and substantially colorless CPC-Acid can be distilled continuously from, the heated vessel.

Crude, off-color CPC-Acid obtained by contacting cyclopropanecarboxaldehyde with molecular oxygen can be subjected directly to our novel color removal process prior to any purifying distillation step. Optionally, crude, off-color CPC-Acid can be distilled prior the strong acid treatment which usually enhance the efficiency of the decolorizing process when a bed of a polymeric sulfonic acid is used.

The process of the present invention provides a simple and cost effective way for the production of colorless CPC-Acid of high purity without the need for of expensive reagents. The process is carried out under mild conditions with simple product isolation and very limited waste generation.

The process provided by the present invention is further illustrated by the following examples. The purities of the CPC-Acid samples used in the examples was determined by gas chromatographic (GC) analyses performed on a Hewlett-Packard 5890 series II gas chromatography with a 30 meter DB-Wax capillary column. Color measurements were performed on a Hunter Meter Colorquest and reported as platinum-cobalt scale (PCS) values (ASTM Procedure D 1209).

EXAMPLE 1

A mixture of yellow CPC-Acid (200 g, PCS color=102, 99.2% purity) and a polymeric sulfonic acid (Amberlyst-15 resin, 10 g) in a 300 mL flask was heated at 85° C. for 3 hours with stirring. After the removal of the polymeric sulfonic acid, the mixture was distilled under reduced pressure (100 to 110 torr) to give colorless CPC-Acid (192 g, PCS color=1, 99.7% purity).

EXAMPLE 2

A mixture of brown CPC-Acid (200 g, PCS color=>500, 90.0% purity) and a polymeric sulfonic acid (Amberlyst-15 resin, 10 g) was heated in a 300 mL flask at 100° C. for 16 hours with stirring. After the removal of the polymeric sulfonic acid, the mixture was distilled under reduced pressure as in Example 1 to give substantially colorless CPC-Acid (165 g, PCS color=2, 99.7% purity).

EXAMPLE 3

A mixture of yellow CPC-Acid (200 g, PCS color=199, 95.4% purity) and a polymeric sulfonic acid (Amberlyst-15 resin, 10 g) was heated in a 300 mL flask at 85° C. for 3 hours with stirring. After the removal of the polymeric sulfonic acid, the mixture was distilled under reduced pressure as in Example 1 to give colorless CPC-Acid (187 g, PCS color=1, 99.7% purity).

EXAMPLE 4

A mixture of yellow CPC-Acid (200 g, PCS color=102, 99.2% purity) and a perfluorosulfonic acid polymer (Nafion-H resin, 5 g) was heated in a 300 mL flask at 85° C. for 3 hours with stirring. After the removal of the perfluorosulfonic acid polymer, the mixture was distilled under reduced as in Example 1 to give colorless CPC-Acid (188 g, PCS color=2, 99.7% purity).

EXAMPLE 5

A mixture of yellow CPC-Acid (200 g, PCS color=102, 99.2% purity) and toluenesulfonic acid (4 g) was heated in a 300 mL flask at 85° C. for 3 hours with stirring. The mixture was distilled under reduced pressure as in Example 1 to give colorless CPC-Acid (191 g, PCS color=1, 99.7% purity).

EXAMPLE 6

A mixture of yellow CPC-Acid (200 g, PCS color=102, 99.2% purity) and polyphosphoric acid (4 g) was heated in a 300 mL flask at 85° C. for 3 hours with stirring. The mixture was distilled under reduced pressure as in Example 1 to give colorless CPC-Acid (190 g, PCS color=1, 99.8% purity).

EXAMPLE 7

A mixture of brown CPC-Acid (200 g, PCS color=>500, 90.0% purity) and polyphosphoric acid (4 g) was heated in a 300 mL flask at 145° C. for 1 hour with stirring. The mixture was distilled under reduced pressure as in Example 1 to give colorless CPC-Acid (168 g, PCS color=2, 99.7% purity).

EXAMPLE 8

A mixture of brown CPC-Acid (200 g, PCS color=>500, 90.0% purity) and polyphosphoric acid (1.2 g) was heated in a 300 mL flask at 100° C. for 10 hours with stirring. The mixture was distilled under reduced pressure as in Example 1 to give colorless CPC-Acid (172 g, PCS color=1, 99.7% purity).

EXAMPLE 9

A mixture of yellow CPC-Acid (200 g, PCS color=102, 99.2% purity) and sulfuric acid (2 g) was heated in a 300 mL flask at 85° C. for 5 hours with stirring. The mixture was distilled under reduced pressure as in Example 1 to give substantially colorless CPC-Acid (188 g, PCS color=3), 99.5% purity).

EXAMPLE 10

Yellow CPC-Acid (PCS Color=199, 95.4% purity) was fed at the rate of 5 g per minute to the bottom of a jacketed column packed with a polymeric sulfonic acid beads (Amberlyst-15 resin, 50 g). The bed of polymeric sulfonic acid beads was heated by means of steam fed to the column jacket to maintain the average temperature of the bed at about 98° C. A total of 1000 mL of CPC-Acid was passed through the resin bed and was collected from the top of the column. Distillation of the treated CPC-Acid gave colorless CPC-Acid (PCS color=1, 99.7% purity).

COMPARATIVE EXAMPLE 1

Brown CPC-Acid (200 g, PCS color=>500, 90.0% purity) was distilled under reduced pressure (100 to 110 torr to produce a yellow CPC-Acid (168 g, PCS color=101, 99.5% purity). The material used in this example also was used in Example 2.

COMPARATIVE EXAMPLE 2

Yellow CPC-Acid (200 g, PCS color=102, 99.2% purity) was distilled under reduced pressure (100 to 110 torr to produce CPC-Acid (168 g, 99.7% purity) which still had a yellow color (PCS color=91).

The invention has been described in detail with particular reference to preferred embodiments thereof, but it will be understood that variations and modifications can be effected within the spirit and scope of the invention.

We claim:

1. Process for the conversion of off-color cyclopropanecarboxylic acid (CPC-Acid) to CPC-Acid having a platinum-cobalt scale (PCS) color value of less than about 10 by the steps of:

(1) heating off-color CPC-Acid produced by the oxidation of cyclopropanecarboxaldehyde with molecular oxygen with a strong acid; and (2) distilling the mixture of step (1) to obtain CPC-Acid having a color value of less than about 10 PCS as the distillate product;

wherein the color values are measured by ASTM Procedure D 1209.

2. Process according to claim 1 wherein CPC-Acid having a color value of at least 20 PCS is heated at a temperature of about 50° to 150° C. in the presence of a strong acid selected from organic sulfonic acids, phosphoric acid, polyphosphoric acid and sulfuric acid.

3. Process according to claim 2 wherein the amount of acid used is about 0.1 to 5 weight per cent based on the weight of the CPC-Acid present.

4. Process for the conversion of off-color cyclopropanecarboxylic acid (CPC-Acid) having a color value of about 20 to 800 to CPC-Acid having a color value of less than about 10 by the steps of:

(1) heating the off-color CPC-Acid produced by the oxidation of cyclopropanecarboxaldehyde with molecular oxygen with about 0.1 to 5 weight per cent, based on the weight of the CPC-Acid present, of a polymeric sulfonic acid; and (2) distilling the mixture of step (1) to obtain CPC-Acid having a color value of less than about 10 as the distillate product;

wherein the polymeric sulfonic acid is separated from the CPC-Acid prior to step (2) and the color values are measured by ASTM Procedure D 1209.

5. Process according to claim 4 wherein the distillation of step (2) is carried out at a reduced pressure in the range of about 0.5 to 200 torr.

* * * * *